US 8,857,804 B2

(12) United States Patent
Wang et al.

(10) Patent No.: US 8,857,804 B2
(45) Date of Patent: Oct. 14, 2014

(54) CLAMPING JIG, A FRICTION TESTING DEVICE HAVING THE CLAMPING JIG, AND FRICTION TEST METHOD

(75) Inventors: Yi-Chiang Wang, New Taipei (TW); Wen-Hui Shi, New Taipei (TW)

(73) Assignee: Wistron Corporation, New Taipei (TW)

( * ) Notice: Subject to any disclaimer, the term of this patent is extended or adjusted under 35 U.S.C. 154(b) by 361 days.

(21) Appl. No.: 13/357,094

(22) Filed: Jan. 24, 2012

(65) Prior Publication Data

US 2012/0192616 A1 Aug. 2, 2012

(30) Foreign Application Priority Data

Jan. 30, 2011 (CN) .......................... 2011 1 0032674

(51) Int. Cl.
  *G01N 3/00* (2006.01)
  *G01N 19/02* (2006.01)
  *G01N 3/04* (2006.01)
(52) U.S. Cl.
  CPC .......... *G01N 3/04* (2013.01); *G01N 2203/0423* (2013.01); *G01N 19/02* (2013.01)
  USPC ........................................... 269/111; 269/44
(58) Field of Classification Search
  CPC ........ B25B 1/2489; B25B 11/02; B25B 5/166
  USPC ......... 269/1–9, 109, 111–126, 287, 318, 319, 269/45, 56, 58, 60, 63, 71
  See application file for complete search history.

(56) References Cited

U.S. PATENT DOCUMENTS

| 86,740 | A | * | 2/1869 | Dunaway | 269/113 |
|---|---|---|---|---|---|
| 1,000,725 | A | * | 8/1911 | Duus | 269/109 |
| 1,490,608 | A | * | 4/1924 | Gilmour | 269/104 |
| 2,552,094 | A | * | 5/1951 | Hamon et al. | 269/156 |
| 4,648,585 | A | * | 3/1987 | Yang | 269/104 |

(Continued)

FOREIGN PATENT DOCUMENTS

| CN | 101412219 A | 4/2009 |
|---|---|---|
| CN | 201293695 Y | 8/2009 |

(Continued)

OTHER PUBLICATIONS

Official Action issued Jul. 29, 2013, by the State Intellectual Property Office of the People's Republic of China, in related Chinese Patent Application No. 201110032674.6, with partial English translation (10 pages).

(Continued)

*Primary Examiner* — Lee D Wilson
*Assistant Examiner* — Tyrone V Hall, Jr.
(74) *Attorney, Agent, or Firm* — Osha Liang LLP

(57) ABSTRACT

A clamping jig for clamping a test object includes a first clamping member extending in a left-right direction, two second clamping members connected to and extending transversely of the first clamping member and spaced apart from each other in the left-right direction, and a third clamping member connected to and extending transversely of the second clamping members. The third clamping member is movable along the second clamping members in a front-rear direction to adjust a distance between the first and third clamping members. The first, second, and third clamping members are adapted to clamp therebetween the test object.

26 Claims, 18 Drawing Sheets

(56) References Cited

U.S. PATENT DOCUMENTS

| | | | | |
|---|---|---|---|---|
| 4,821,393 A * | 4/1989 | Spigarelli | | 29/283 |
| 5,730,433 A * | 3/1998 | Veres | | 269/41 |
| 6,112,783 A * | 9/2000 | Newman | | 144/144.52 |
| 6,182,371 B1 * | 2/2001 | Newman | | 33/194 |
| 6,446,951 B2 * | 9/2002 | Nuxoll et al. | | 269/118 |
| 6,811,131 B2 * | 11/2004 | Kuo | | 248/346.03 |
| 6,956,563 B2 | 10/2005 | Yamashita | | |
| 7,422,202 B2 * | 9/2008 | Wu | | 269/303 |
| 2011/0024962 A1 * | 2/2011 | Zhang | | 269/107 |

FOREIGN PATENT DOCUMENTS

| | | |
|---|---|---|
| CN | 101762292 A | 6/2010 |
| TW | 286642 | 9/1996 |
| TW | 1238970 | 9/2005 |

OTHER PUBLICATIONS

Espacenet English Abstract for Chinese Publication No. CN201293695, published Aug. 19, 2009 (1 page).

Espacenet English Abstract for Chinese Publication No. CN101412219, published Apr. 22, 2009 (2 pages).

Espacent English Abstract for Chinese Publication No. CN101762292, published Jun. 30, 2012 (1 page).

Taiwanese patent, Utility Model Patent No. M357607, issued May 21, 2009 (Taiwan Application No. TW-098200984 filed Jan. 19, 2009), together with an abridged English translation (16 pages).

Official Action isued Jun. 12, 2014, by the Taiwan Patent Office in corresponding Taiwan Patent Application No. 100103922, with partial English translation (14 pages).

\* cited by examiner

CLAMPING JIG, A FRICTION TESTING DEVICE HAVING THE CLAMPING JIG, AND FRICTION TEST METHOD

CROSS-REFERENCE TO RELATED APPLICATION

This application claims priority of Chinese Application No. 201110032674.6, filed on Jan. 30, 2011, the disclosure of which is incorporated herein by reference.

BACKGROUND OF THE INVENTION

1. Field of the Invention

This disclosure relates to a clamping jig, and more particularly to a clamping jig for clamping a test object, a friction testing device having the clamping jig, and a friction test method.

2. Description of the Related Art

A friction testing device, as disclosed in Taiwanese Patent No. M357607, places a test object in a groove of a holding plate, after which a press plate is moved downward by an elevating mechanism so that a friction element and the test object are in contact with each other. Subsequently, a movable plate moves the holding plate and the test object reciprocally along a guide rail set, so that the test object is in frictional contact with and moves relative to the friction element. Through this configuration, a rub resistance value of the test object can be determined.

Since the size of the groove in the holding plate is fixed, the holding plate can only hold a test object having dimensions fitting that of the groove, but cannot hold different specifications and dimensions of test objects. Hence, use of the aforesaid friction testing device is limited.

SUMMARY OF THE INVENTION

A main object of the present disclosure is to provide a clamping jig that can clamp different specifications and dimensions of test objects to increase flexibility of use of the present disclosure.

Another object of the present disclosure is to provide a friction testing device having a clamping jig. Through the clamping jig which can clamp different specifications and dimensions of test objects, friction tests of the test objects with different specifications and dimensions can be performed.

Still another object of the present disclosure is to provide a friction testing device having a clamping jig, roller units, and a push mechanism. Through the presence of the roller units, friction between the clamping jig and a top frictional face of a working platform can be reduced to enhance accuracy of friction testing a test object. The push mechanism is provided to move the clamping jig and the test object reciprocally in any direction to simulate a moving direction of the test object during an actual use thereof, thereby enhancing reliability of the test object.

An additional object of the present disclosure is to provide a friction test method. Through the use of a clamping jig which can clamp different specifications and dimensions of test objects, friction tests of the test objects with different specifications and dimensions can be performed, thereby increasing flexibility of use of the present disclosure.

The purpose of the present disclosure and the solution to the conventional technical problems are achieved through employment of the below technical means. According to one aspect of this disclosure, a clamping jig for clamping a test object comprises a first clamping member extending in a left-right direction, two second clamping members connected to and extending transversely of the first clamping member and spaced apart from each other in the left-right direction, and a third clamping member connected to and extending transversely of the second clamping members. The third clamping member is movable along the second clamping members in a front-rear direction to adjust a distance between the first and third clamping members. The first, second, and third clamping members are adapted to clamp therebetween the test object.

The purpose of the present disclosure and the solution to the conventional technical problems may also be achieved through employment of the below technical means.

One of the second clamping members is movable relative to the first clamping member and the third clamping member in the left-right direction to adjust a distance between the two second clamping members.

The clamping jig further comprises a plurality of spaced-apart roller units attached to bottom ends of the first and second clamping members.

The clamping jig further comprises two first positioning elements to position the third clamping member on the second clamping members, and a second positioning element to position said one of the second clamping members on the first clamping member.

The third clamping member has an elongated guide hole extending in the left-right direction. Each second clamping member extends through the guide hole to intersect the third clamping member, and includes an elongated positioning hole that extends in the front-rear direction. Each first positioning element extends through the positioning hole, and positions the third clamping member to one of the second clamping members.

The first clamping member includes a plurality of screw holes extending therethrough in a top-bottom direction and spaced apart from each other in the left-right direction. Said one of the second clamping members further includes a through hole alignable with one of the screw holes in the first clamping member. The second positioning element is configured as a screw that engages one of the screw holes in the first clamping member and that extends through the through hole in the one of the second clamping members.

The through hole in said one of the second clamping members is elongated in the left-right direction. Said one of the second clamping members is movable relative to the second positioning element along an extending direction of the through hole. The first clamping member further includes an elongated guide groove that receives one end of each of the second clamping members and that communicates with the screw holes in the first clamping member and the through hole in the one of the second clamping members. The guide groove in the first clamping member and the guide hole in the third clamping member are at a same height from the working platform.

Each second clamping member includes a plurality of screw holes spaced apart from each other in a length direction of the second clamping members. The third clamping member has left and right ends respectively overlapping the second clamping members, and includes two passage holes formed respectively in the left and right ends. The clamping jig further includes two first positioning elements. Each first positioning element is configured as a screw that extends through one of the passage holes and that engages a selected one of the screw holes in one of the second clamping members, which is aligned with said one of the passage holes.

Each of the passage holes is elongated in a direction that is transverse to a length direction of the third clamping member so that the third clamping member is movable relative to the first positioning elements along the direction of the passage holes.

According to another aspect of this disclosure, a friction testing device for a test object comprises a working platform, a clamping jig, and a push mechanism. The working platform includes a top frictional face. The clamping jig has a clamping frame that is disposed movably on the top frictional face and that includes a first clamping member extending in a left-right direction, two second clamping members connected to and extending transversely of the first clamping member and spaced apart from each other in the left-right direction, and a third clamping member connected to and extending transversely of the second clamping members. The third clamping member is movable along the second clamping members in a front-rear direction to adjust a distance between the first and third clamping members. The first, second, and third clamping members are adapted to clamp therebetween the test object. The push mechanism is provided to move reciprocally the clamping jig on the top frictional face.

According to still another aspect of this disclosure, a friction test method comprises: (A) moving a movable part of a clamping jig relative to a fixed part of the clamping jig so that a test object is placed between the movable and fixed parts of the clamping jig; (B) positioning the movable part to the fixed part to clamp the test object; (C) activating a push mechanism that is connected to the clamping jig to move reciprocally the clamping jig and the test object on a top frictional face of a working platform; and (D) inspecting the test object and the top frictional face after movement of the clamping jig is stopped.

In step (A), the movable part is movable forward and rearward to adjust a distance between the movable part and a first clamping member of the fixed part, and the fixed part further has two second clamping members that are movable leftward and rightward to adjust a distance therebetween. In step (B), the second clamping members are fixed to the first clamping member and the movable part is fixed to the second clamping members.

In step C, the clamping jig is slidable on the top frictional face through a plurality of roller units.

Through the aforesaid technical means, the advantages and efficiencies of the friction testing device having the clamping jig according to the present disclosure reside in that through the clamping jig which can clamp different specifications and dimensions of test objects, the flexibility of use of the present disclosure can be increased, so that friction tests on test objects with different specifications and dimensions can be performed. Further, through the presence of the roller units, friction between the clamping jig and the top frictional face of the working platform can be reduced, so that influence of friction on foot pads of the test object during testing can be lowered, thereby enhancing accuracy of friction testing. Moreover, a moving direction of the test object during an actual use thereof can be simulated to ensure that the testing method conforms to an actual use condition and to enhance reliability of the test object.

BRIEF DESCRIPTION OF THE DRAWINGS

Other features and advantages of the present disclosure will become apparent in the following detailed description of the embodiments of the disclosure, with reference to the accompanying drawings, in which.

DETAILED DESCRIPTION OF THE PREFERRED EMBODIMENTS

Figure 1:
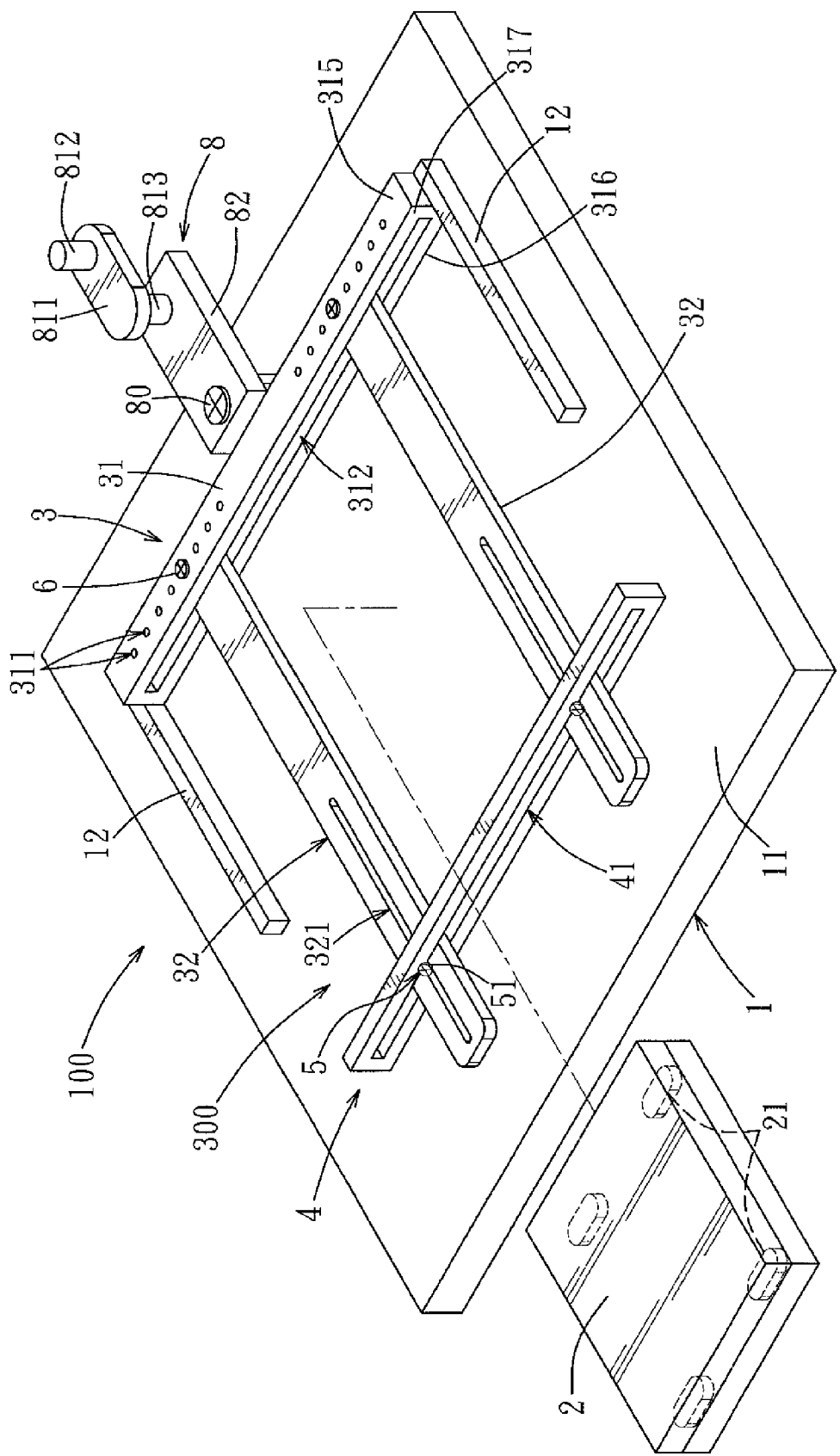
FIG. 1 is a perspective view of a friction testing device having a clamping jig according to the first embodiment of the present disclosure.
Figure 2:
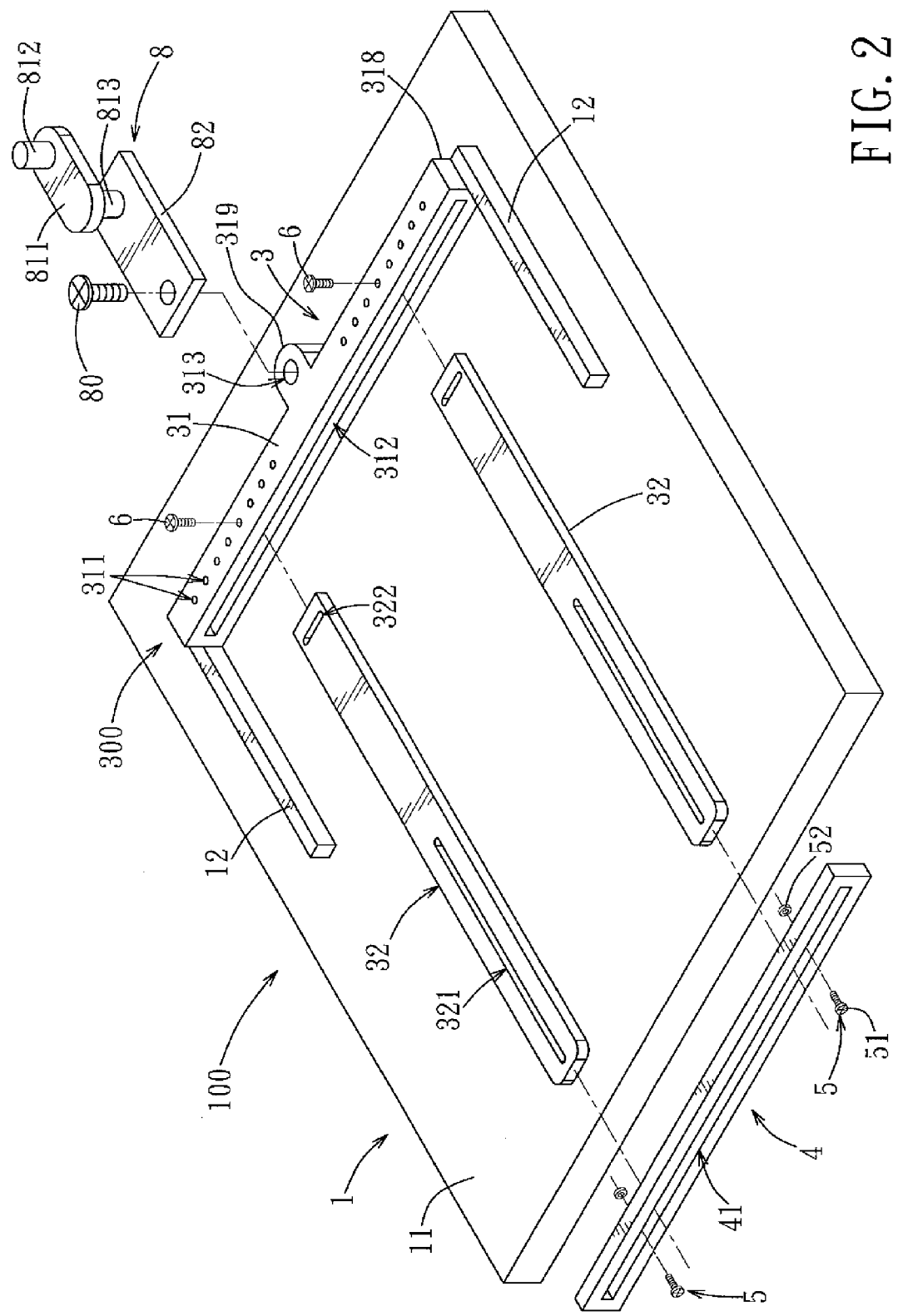
FIG. 2 is an exploded perspective view of the first embodiment.
Figure 3:
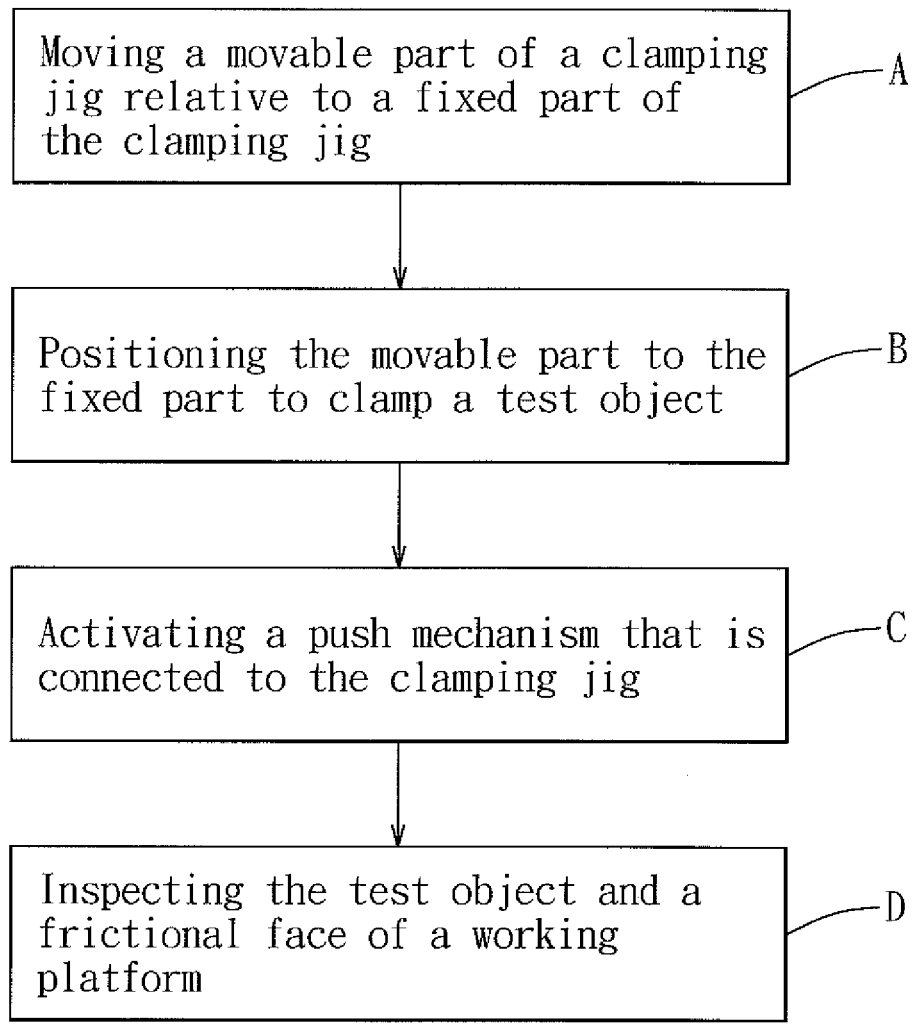
FIG. 3. is a flow chart, illustrating steps involved in a friction test method according to the first embodiment.
Figure 4:
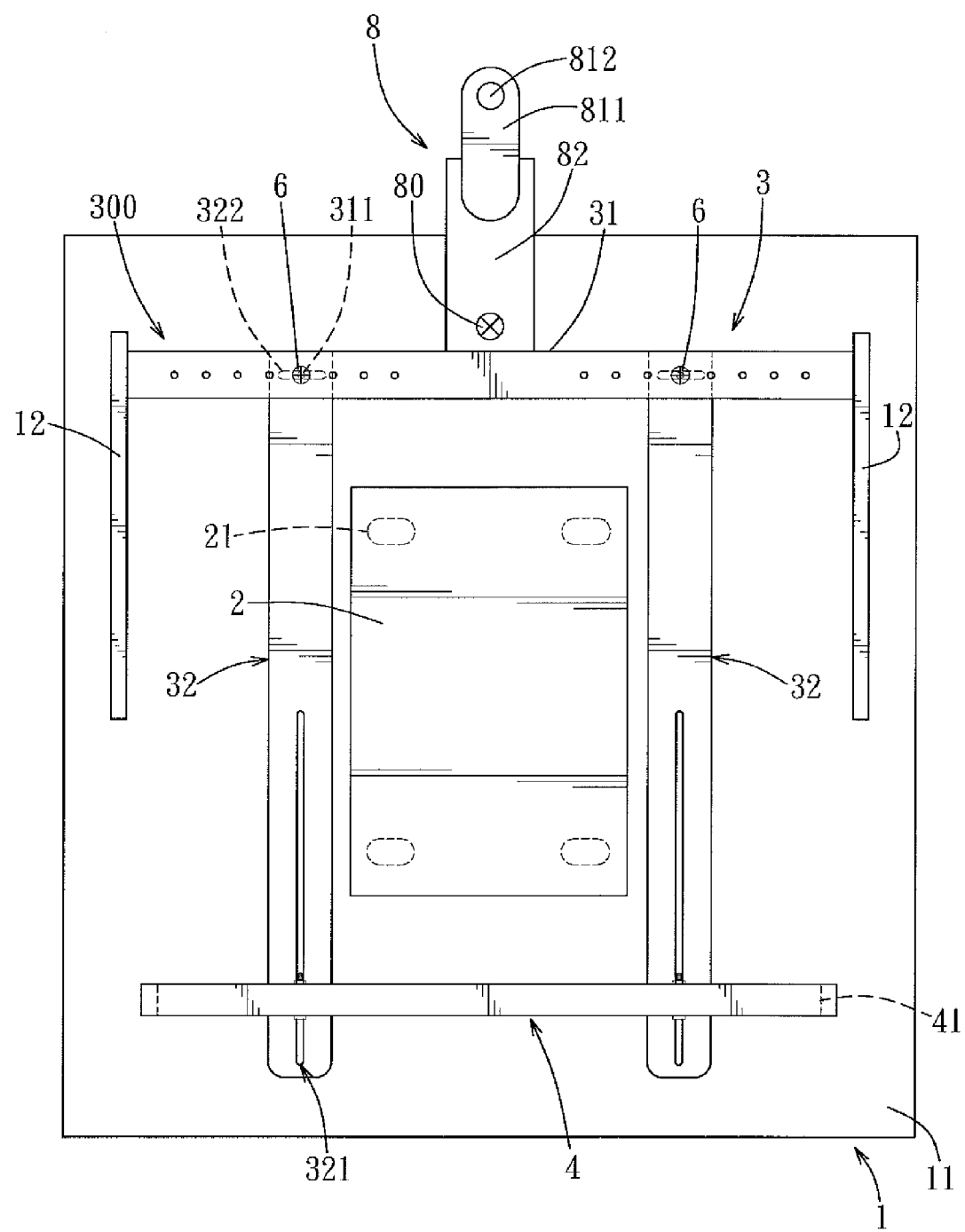
FIG. 4 is a schematic top view of the first embodiment in an assembled state.
Figure 5:
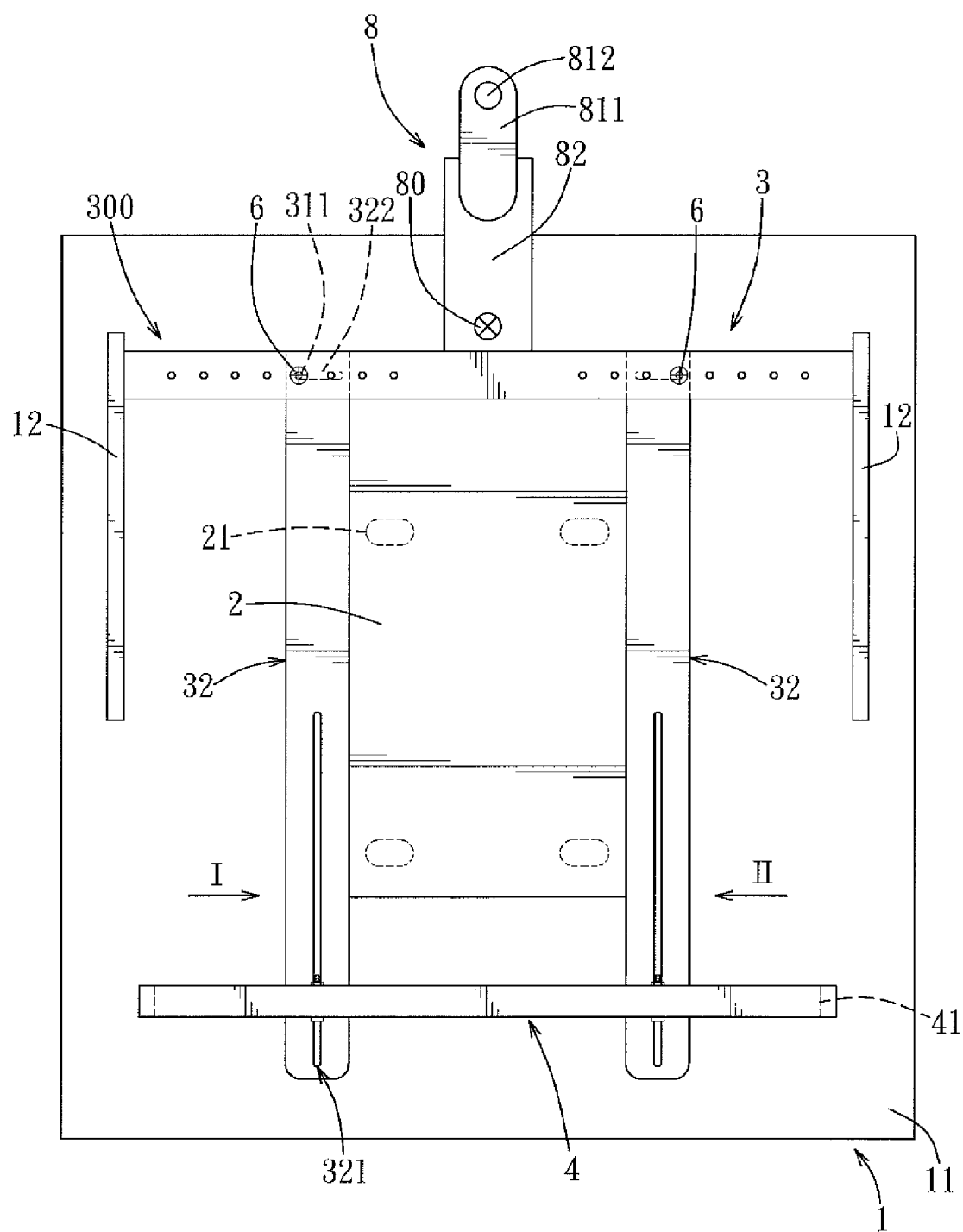
FIG. 5 is a view similar to FIG. 4, but illustrating two second clamping members clamping respectively left and right sides of a test object.
Figure 6:
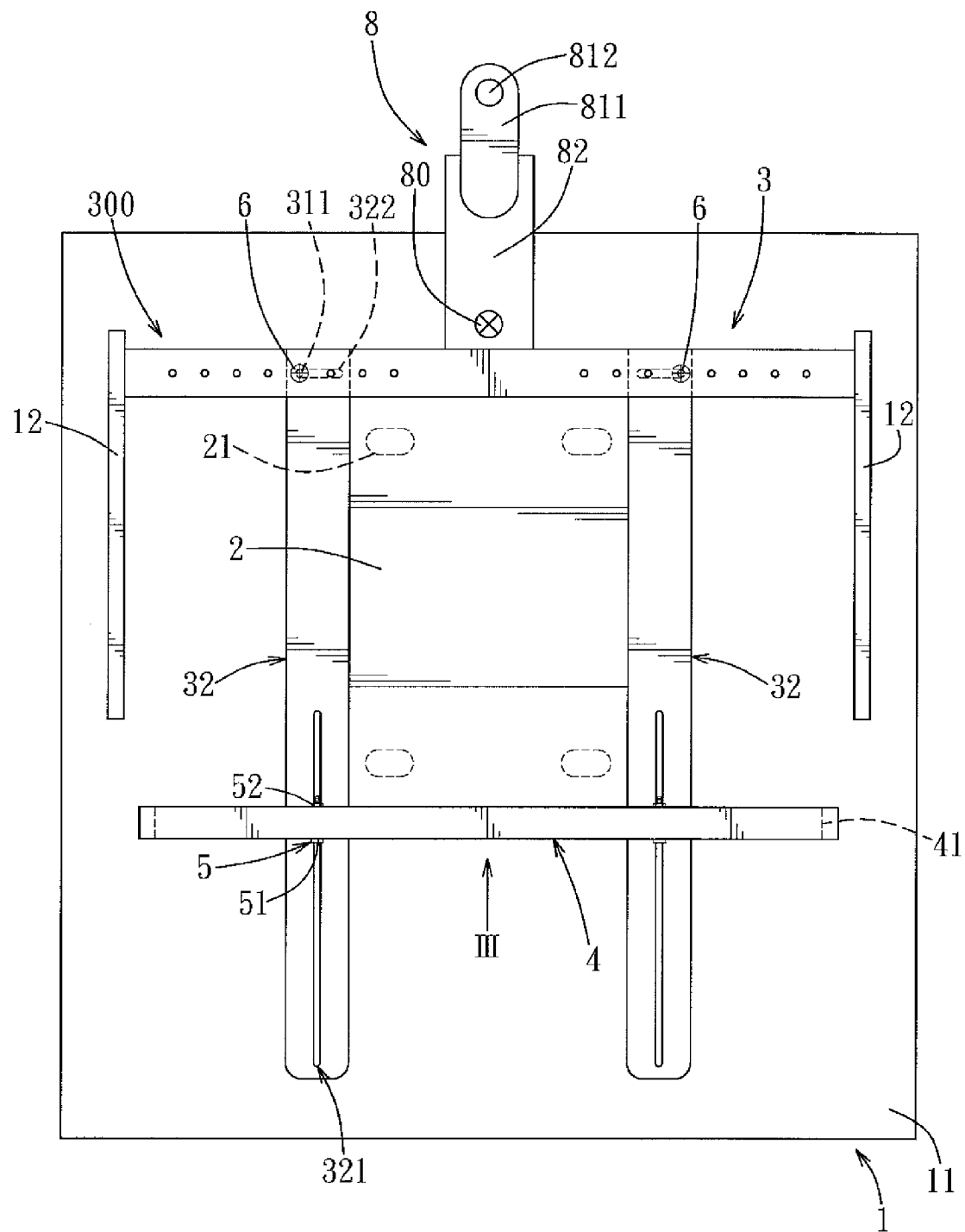
FIG. 6 is a view similar to FIG. 5, but illustrating a third clamping member and a first clamping member clamping respectively front and rear sides of the test object.

The above-mentioned and other technical contents, features, and effects of this disclosure will be clearly presented from the following detailed description of the five embodiments in coordination with the reference drawings. Through description of the concrete implementation method, the technical means employed and the effectiveness to achieve the predetermined purposes of the present disclosure will be thoroughly and concretely understood. However, the enclosed drawings are used for reference and description only, and are not used for limiting the present disclosure.

Before this disclosure is described in detail, it should be noted that, in the following description, similar elements are designated by the same reference numerals.

Referring to FIGS. 1 to 7, a friction testing device 100 according to the first embodiment of the present disclosure comprises a working platform 1, a clamping jig 300, and a push mechanism 8. Through these components, a friction test on a test object can be performed.

In this embodiment, a friction test on a plurality of foot pads 21 provided on a bottom side of a test object 2 and made of rubber or silicone is exemplified. It is inspected whether the foot pads 21, after the friction test, have deformed, cracked or damaged, or have separated from the test object 2. The test object 2 may be an electronic device, such as a notebook computer, a tablet computer, or a monitor, having foot pads 21. However, the test is not limited to the foot pads 21, any test object 2 that requires friction testing to determine the degree of damage of its appearance due to friction may use the friction testing device 100.

The working platform 1 includes a top frictional face 11, left and right sides, front and rear sides, and a limit unit disposed on the top frictional face 11. In this embodiment, the limit unit includes two guide rails 12 extending in a front-rear direction and spaced apart in a left-right direction.

The clamping jig 300 has a clamping frame 3 disposed movably on the top frictional face 11 to clamp the test object 2. The clamping frame 3 includes a first clamping member 31, two second clamping members 32, and a third clamping member 4. The first clamping member 31 is rectangular, extends in the left-right direction, and is disposed in proximity to the rear side of the working platform 1. The first clamping member 31 has left and right ends in sliding contact with the guide rails 12, respectively. The second clamping members 32 are connected to and extend transversely from a front end of the first clamping member 31, and are spaced apart from each other in the left-right direction. Each second clamping member 32 has a rectangular shape. The third clamping member 4 has a rectangular shape, and extends in the left-right direction. The third clamping member 4 is connected to and extends transversely of the second clamping members 32, and is movable along the second clamping members 32 in the front-rear direction. Through this configuration, a distance between the first clamping member 31 and the third clamping member 4 can be adjusted, so that the first, second, and third clamping members 31, 32, 4 can clamp therebetween the test object 2. Because the third clamping member 4 is movable, test objects having different specifications and dimensions may be clamped between the first, second, and third clamping members 31, 32, 4 of the clamping frame 3.

Figure 7:
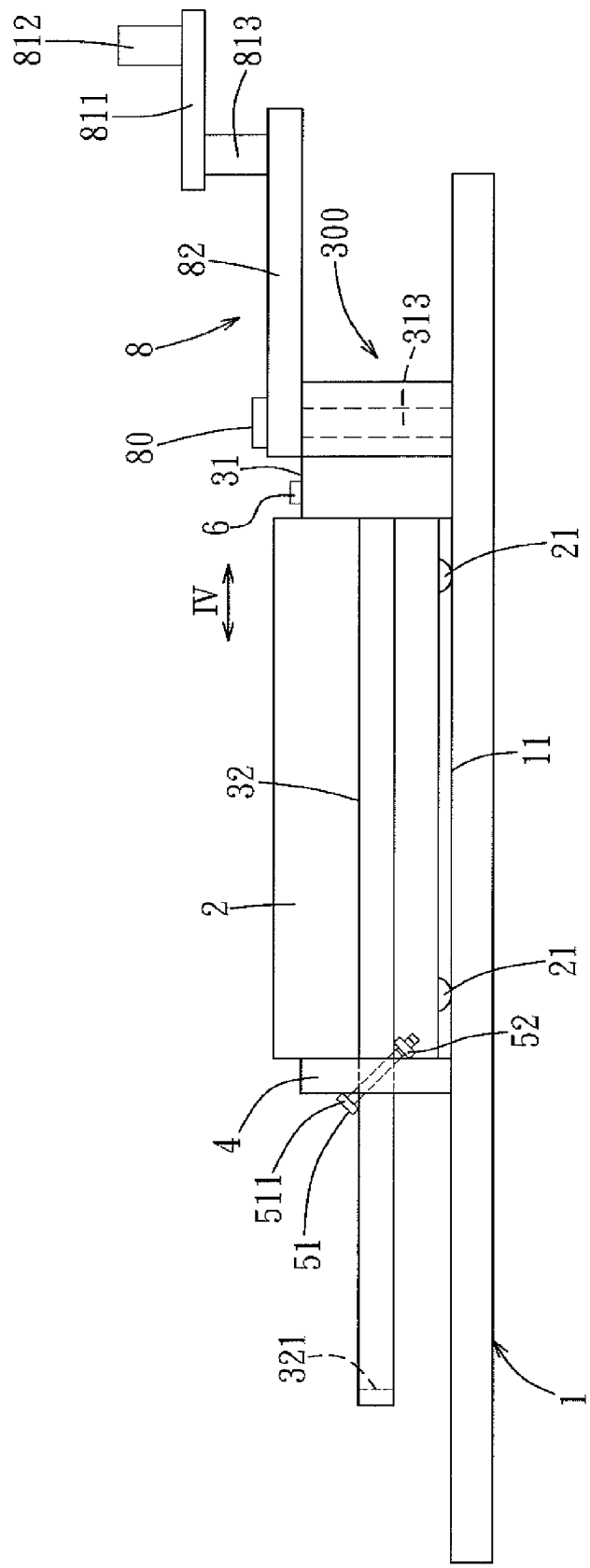
FIG. 7 is a schematic side view of the first embodiment.

The clamping jig 300 further includes two first positioning elements 5 to position the third clamping member 4 on the second clamping members 32 so that the third clamping member 4 cannot move relative to the second clamping members 32. As such, the first, second, and third clamping members 31, 32, 4 can stably clamp therebetween the test object 2. In this embodiment, the third clamping member 4 includes an elongated guide hole 41 extending in the left-right direction. Each second clamping member 32 extends through the guide hole 41 to intersect the third clamping member 4, and includes an elongated positioning hole 321 that extends in the front-rear direction and that communicates with the guide hole 41. Each first positioning element 5 includes a screw 51 that extends through the guide hole 41 and the positioning hole 321 in a respective second clamping member 32 and that has a screw head 511, and a nut 52 (see FIGS. 2 and 7) engaged to the screw 51 opposite to the screw head 511. The third clamping member 4 is engaged between the screw head 511 and the nut 52, as shown in FIG. 7. Through this configuration, the third clamping member 4 can be positioned fixedly to the second clamping members 32. It should be noted that the positioning method of the third clamping member 4 on the second clamping members 32 is not limited to the disclosed embodiment. The third clamping member 4 may also be positioned to each second clamping member 32 using a complementary groove and protrusion engaging method.

To clamp test objects of different specifications and dimensions and flexible use of the clamping jig 300, in this embodiment, the second clamping members 32 are movable in the left-right direction relative to the first and third clamping members 31, 4. As such, following the specifications and dimensions of the test object 2, a distance between the two second clamping members 32 can be adjusted, so that the second clamping members 32 can clamp left and right sides of the test object 2. The clamping jig 300 further includes two second positioning elements 6 to position the second clamping members 32 on the first clamping member 31. The first clamping member 31 further includes a plurality of screw holes 311 extending therethrough in a top-bottom direction and spaced apart from each other in the left-right direction. Each second clamping member 32 further includes a through hole 322 formed in a rear end thereof and spaced apart from the positioning hole 321. The through hole 322 is alienable with a selected one of the screw holes 311. Each second positioning element 6 is configured as a screw that engages a selected one of the screw holes 311 and that extends through the through hole 322 in the respective second clamping member 32.

Preferably, the through hole 322 in each second clamping member 32 is elongated in the left-right direction so that each second clamping member 32 is movable relative to a respective second positioning element 6 along an extending direction of the through hole 322. Hence, each second clamping member 32 can be adjusted slightly within the length of the through hole 322.

It is particularly noted that the second clamping members 32 may be designed such that only one of the second clamping members 32 is movable relative to the first clamping member 31 and the third clamping member 4, and the other one is fixed to the first clamping member 31. The distance between the two second clamping members 32 can be similarly adjusted. In this case, there is only one second positioning element 6 to position the movable second clamping member 32 on the first clamping member 31.

The first clamping member 31 further includes an elongated guide groove 312 that extends rearwardly from a front wall 317 thereof, that extends in the left-right direction, that receives the rear ends of the second clamping members 32, and that communicates with the screw holes 311 in the first clamping member 31 and the through holes 322 in the second clamping members 32. The guide groove 312 and the guide hole 41 are at a same height from the working platform 1. Through this configuration, the second clamping members 32 have front ends movable within the guide hole 41, and the rear ends movable within the guide groove 312. Further, because the guide groove 312 communicates with the screw holes 311, each second positioning element 6 can engage a selected one of the screw holes 311 in a top wall 315 of the first clamping member 31, and can extend through the guide groove 312 and the through hole 322 in the respective second clamping member 32 to engage a corresponding one of the screw holes 311 in a bottom wall 316 of the first clamping member 31, thereby positioning each second clamping member 32 to the first clamping member 31.

The push mechanism 8 is connected to the clamping jig 300 to move reciprocally the clamping jig 300 and the test object 2 on the top frictional face 11 of the working platform 1. In this embodiment, the push mechanism 8 includes a connecting rod 82 having opposite front and rear ends, an offset shaft 813 connected rotatably to the rear end of the connecting rod 82, a web 811 having a front end connected to a top end of the offset shaft 813, and a rotary shaft 812 projecting from a rear end of the web 811. The front end of the connecting rod 82 is connected to the first clamping member 31 by engaging a screw 80 to a connecting hole 313 in a lug 319 that projects rearwardly from a rear wall 318 of the first clamping member 31. The rotary shaft 812 is connected to a drive unit (riot shown), such as a motor, and is driven by the same to rotate. When the rotary shaft 812 rotates, the web 811, the offset shaft 813, and the connecting rod 82 move along with the rotary shaft 812, thereby moving the clamping jig 300 to-and-fro along the top frictional face 11 of the working platform 1. Alternatively, the push mechanism 8 may be a hydraulic cylinder or another similar structure. Through the push mechanism 8 that moves the clamping jig 300 forward and rearward repeatedly, the clamping jig 300, in turn, can move the test object 2 to-and-fro on the top frictional face 11, so that the foot pads 21 of the test object 2 are in frictional contact with the top frictional face 11. It should be noted that the number of times the push mechanism 8 moves the clamping jig 300 forward and rearward repeatedly along the top frictional face 11 can be set depending upon the actual requirement. For example, it may be set to 2500 times, 5000 times, or 10000 times.

Below is a detailed description of a friction test method of the friction testing device 100 in conjunction with FIGS. 3 to 7. The friction test method includes steps (A-D).

Initially, the test object 2 is placed on the top frictional face 11 of the working platform 1 between the second clamping members 32 and between the first and third clamping members 31, 4. The below steps are performed afterwards.

In step (A), the third clamping member 4 is moved along the second clamping members 32 toward the first clamping member 31 so that the first, second, and third clamping members 31, 32, 4 can clamp therebetween the test object 2. In this step, the two second clamping members 32 are moved toward each other in the direction of arrows (I, II), respectively, so as to clamp respectively the left and right sides of the test object 2. The third clamping member 4 is then moved in the direction of arrow (III) to push the test object 2 against the first clamping member 31, so that the front and rear sides of the test object 2 can be clamped respectively by the first and third clamping members 31, 4.

In step (B), the third clamping member 4 is fixed to the second clamping members 32. In this step, each second positioning element 6 is engaged to one of the screw holes 311 in the top wall 315 of the first clamping member 31 that is aligned with the through hole 322 in the respective second clamping member 32, and extends through the through hole 322 in the respective second clamping member 32 to engage the corresponding screw hole 311 in the bottom wall 316 of the first clamping member 31, thereby positioning the rear end of the respective second clamping member 32 on the first clamping member 31. Afterwards, the screw 51 of each first positioning element 5 is inserted through the guide hole 41 in the third clamping member 4 and the positioning hole 321 in the respective second clamping member 32, and the nut 52 of each first positioning element 5 is engaged to the screw 51 of the respective first positioning element 5, thereby positioning the third clamping member 4 to the front end of the respective second clamping member 32. At this time, the screw head 511 of the screw 51 of each first positioning element 5 abuts against a front end of the third clamping member 4 and a top end of the respective second clamping member 32, and the nut 52 abuts against a rear end of the third clamping member 4 and a bottom end of the respective second clamping member 32.

In step (C), the push mechanism 8 that is connected to the clamping jig 300 is activated to move reciprocally the clamping jig 300 and the test object 2 on the top frictional face 11 of the working platform 1 in the direction of arrow (IV), as shown in FIG. 7. Since the left and right ends of the first clamping member 31 are in sliding contact with the respective guide rails 12, the clamping jig 300 is restricted by the guide rails 12 to move the test object 2 in the front-rear direction along the top frictional face 11 to satisfy a friction test condition for the test object 2 moving in a single direction.

In step (D), the clamping jig 300 is stopped, and the test object 2 and the top frictional face 11 are inspected. By stopping the operation of the push mechanism 8, the clamping jig 300 is stopped from moving the test object 2 on the top frictional face 11. Afterwards, the first and second positioning elements 5, 6 are loosened to adjust positions of the third and second clamping members 4, 32, so that the test object 2 can be removed from the clamping jig 300, and the foot pads 21 thereof are inspected to see if they have deformed, cracked or damaged, or have been separated from the test object 2. As such, the quality of the foot pads 21 can be determined whether or not it can pass the standard requirement.

In this embodiment, because the distance of the third clamping member 4 is adjustable forward and rearward relative to the first clamping member 31, and because the distance between the two second clamping members 32 is adjustable leftward and rightward relative to each other, the clamping jig 300 can clamp test objects of different specifications and dimensions to perform a friction test. Further, the clamping jig 300 moves the test object 2 without applying additional load to the test object 2, so that the test results on the foot pads 21 of the test object 2 can be accurate.

Figure 8:
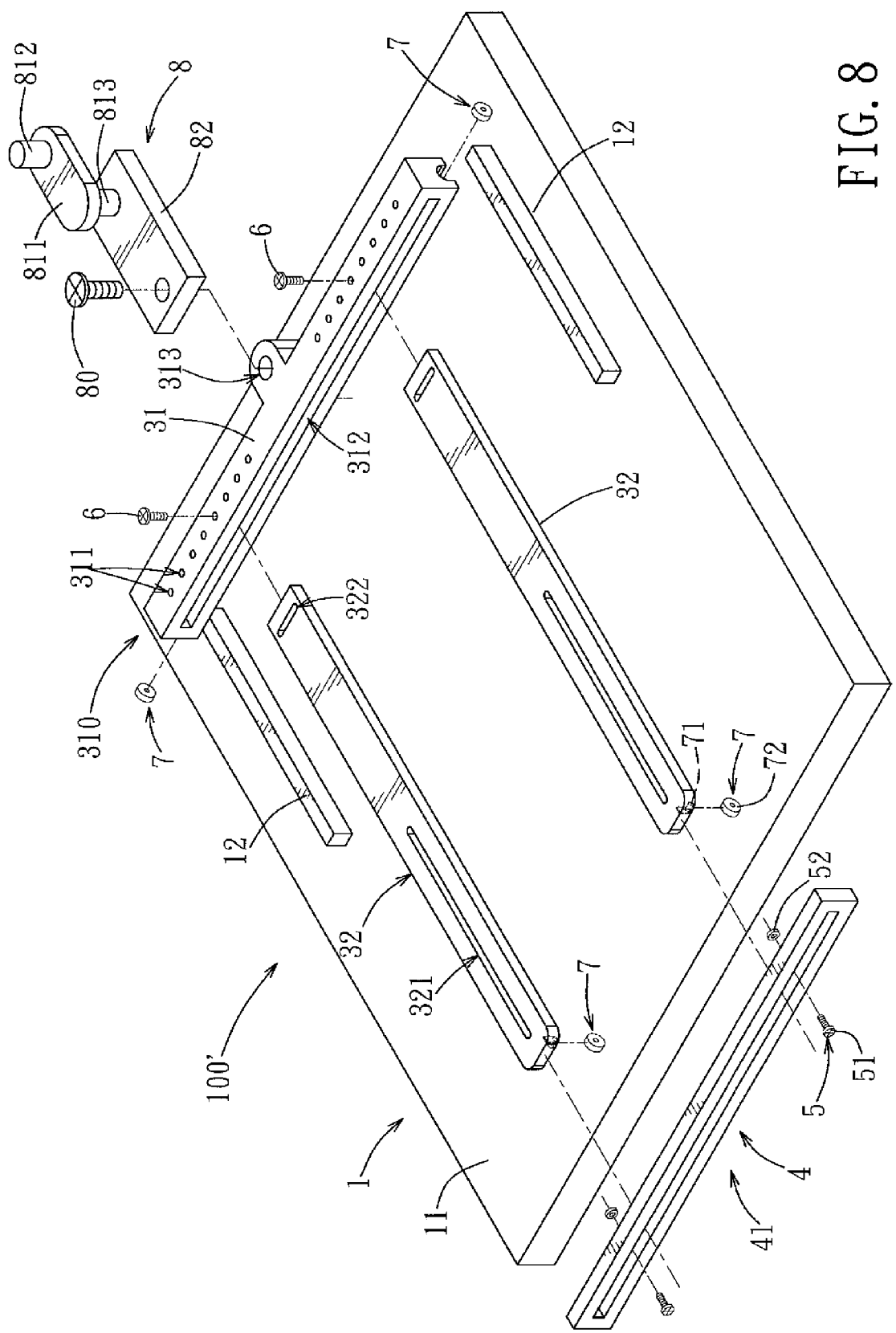
FIG. 8 is an exploded perspective view of a friction testing device having a clamping jig according to the second embodiment of the present disclosure.
Figure 9:
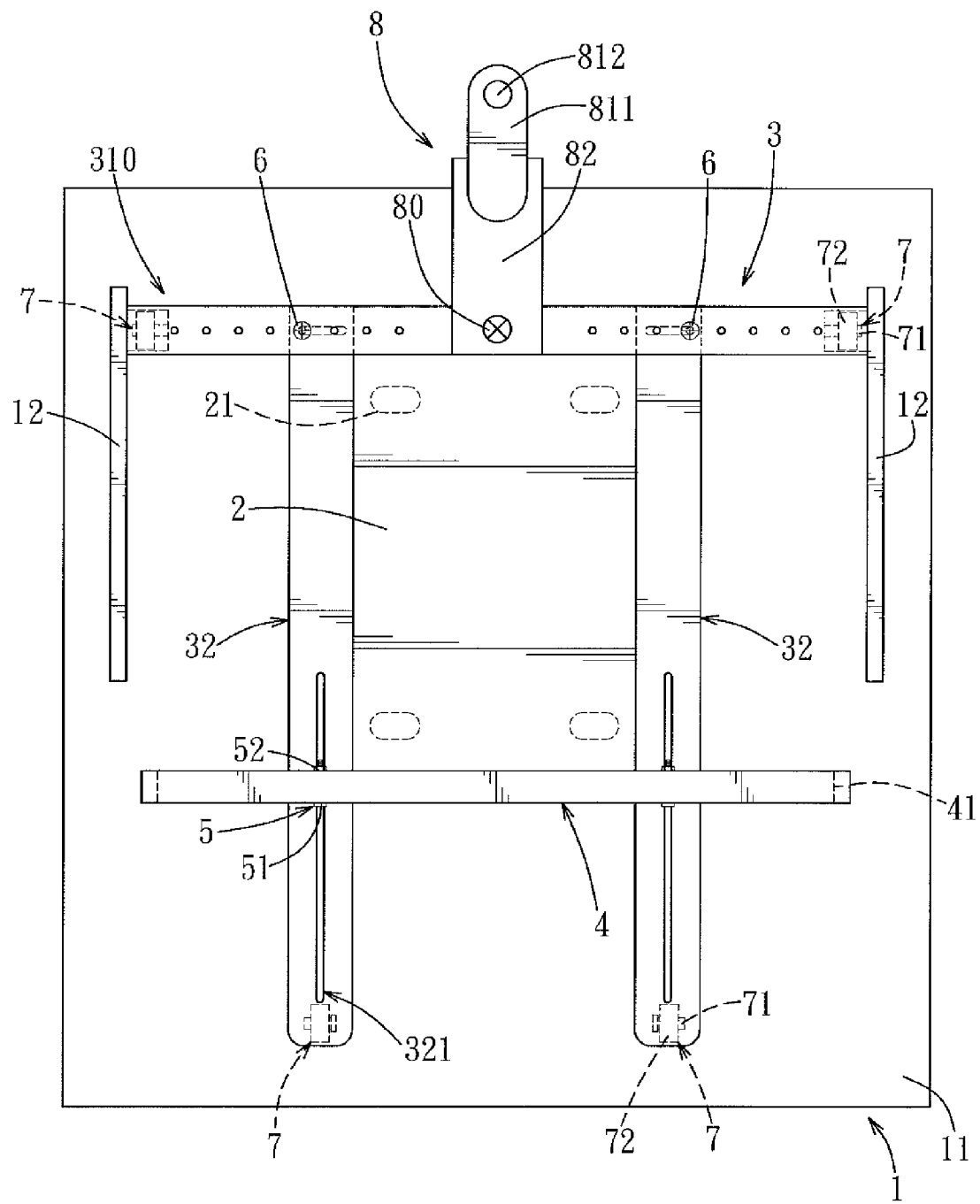
FIG. 9 is a schematic top view of the second embodiment in an assembled state.

Referring to FIGS. 8 and 9, a friction testing device 100' according to the second embodiment of the present disclosure has a structure and an operating method similar to that described in the first embodiment. The difference between the first and second embodiments resides in that the clamping jig 310 further includes a plurality of spaced-apart roller units 7 attached to a bottom side of the clamping frame 3.

In this embodiment, there are four roller units 7, two of which are attached to a bottom side of the first clamping member 31 and the other two of which are attached respectively to bottom sides of the second clamping members 32. Each roller unit 7 includes a rotary shaft 71 connected to one of the first and second clamping members 31, 32 and extending in a left-right direction, and a roller 72 sleeved rotatably on the rotary shaft 71. When the push mechanism 8 moves the clamping jig 310 to-and-fro on the top frictional face 11, the clamping jig 310, in turn, moves the test object 2 along a single direction. Through the configuration of the roller units 7, a frictional force between the clamping jig 310 and the top frictional face 11 can be reduced to lower the effect caused by the frictional force on the foot pads 21 of the test object 2 during testing and to enhance accuracy of the friction test.

Figure 10:
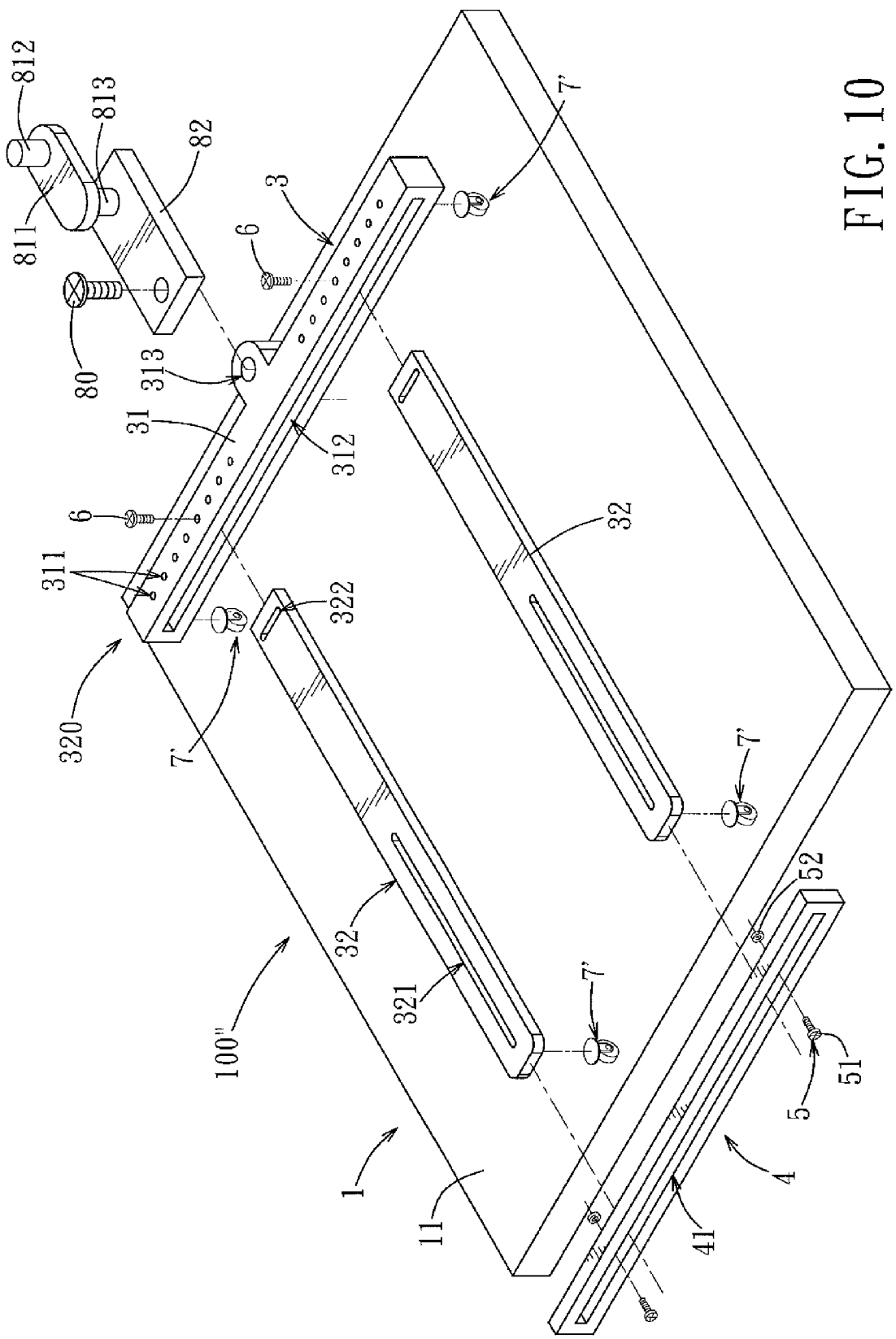
FIG. 10 is an exploded perspective view of a friction testing device having a clamping jig according to the third embodiment of the present disclosure.
Figure 11:
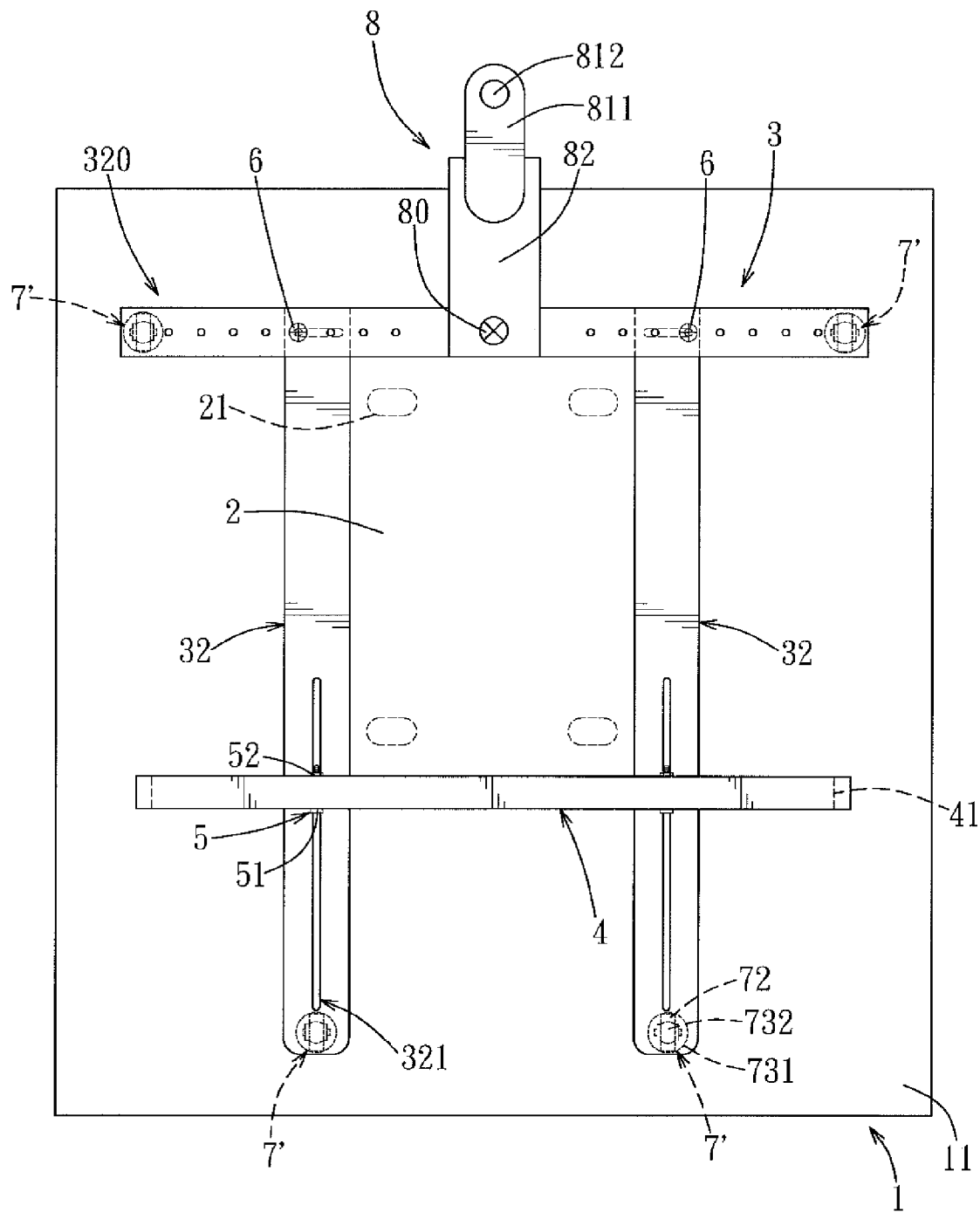
FIG. 11 is a schematic top view of the third embodiment in an assembled state.
Figure 12:
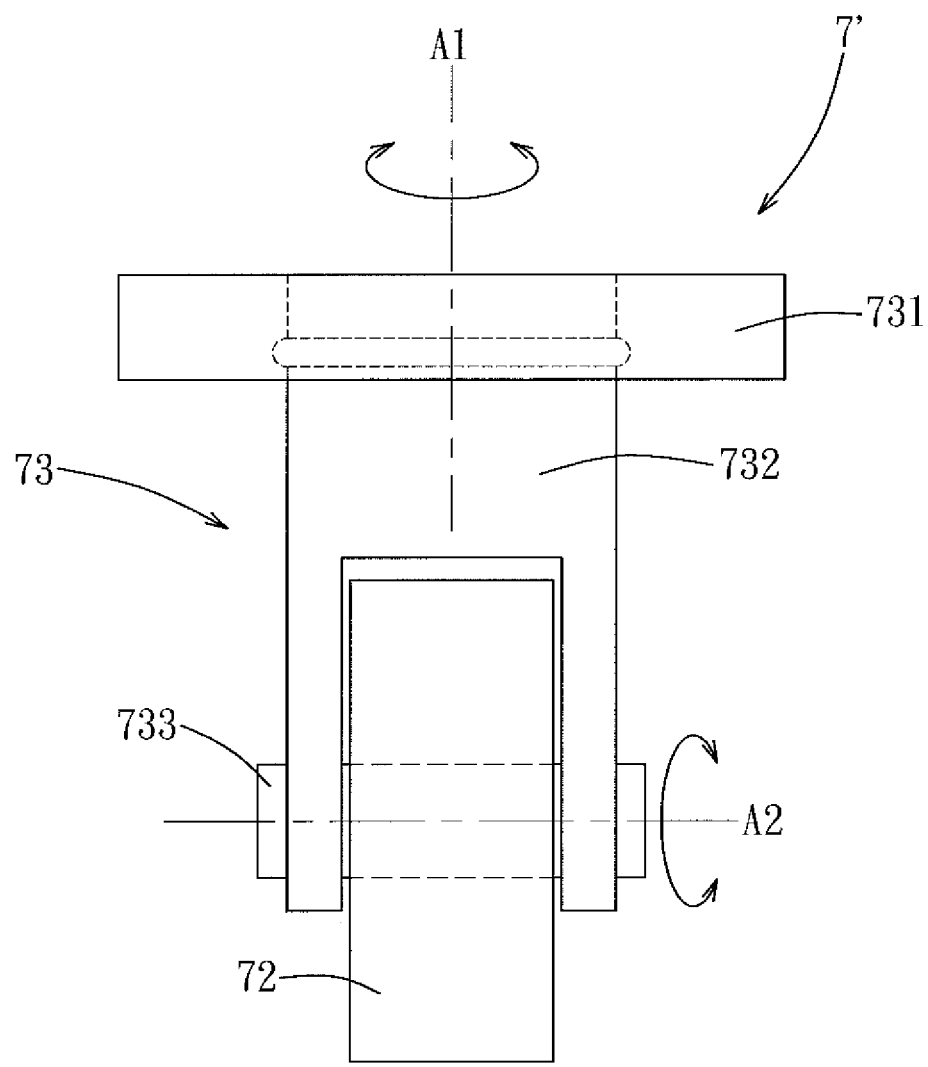
FIG. 12 is an enlarged schematic view of a roller unit of the third embodiment.

Referring to FIGS. 10 to 12, a friction testing device 100" according to the third embodiment of the present disclosure is shown to be similar to the second embodiment. However, in this embodiment, the roller units 7' are configured as swivel rollers. Each swivel roller or roller unit 7' includes a roller 72, and a connector 73 connecting the roller 72 to one of the first and second clamping members 31, 32. The connector 73 includes a connecting disk 731 connected to one of the first and second clamping members 31, 32, a first shaft 732 connected rotatably to the connecting disk 731 and having a first rotation axis (A1) extending in a top-bottom direction, and a second shaft 733 connected to a bottom end of and perpendicular to the first shaft 732 and having a second rotation axis (A2) that is perpendicular to the first rotation axis (A1). The roller 72 is sleeved rotatably on the second shaft 733, and is rotatable about the first and second rotation axes (A1, A2). Through this configuration, the push mechanism 8 can move the clamping jig 320 to any direction, so that the clamping jig 320 can also move the test object 2 along any direction. Through the configuration of the roller units 7', the foot pads 21 of the test object 2 can move to-and-fro on the top frictional face 11 along any direction. This simulates movement of the test object 2 in any direction during actual use thereof, and satisfies a friction test condition for the test object 2 moving in any direction. Further, a frictional force between the clamping jig 320 and the top frictional face 11 can be reduced to lower the effect caused by the frictional force on the foot pads 21 of the test object 2 during testing and to enhance accuracy of the friction test.

Figure 13:
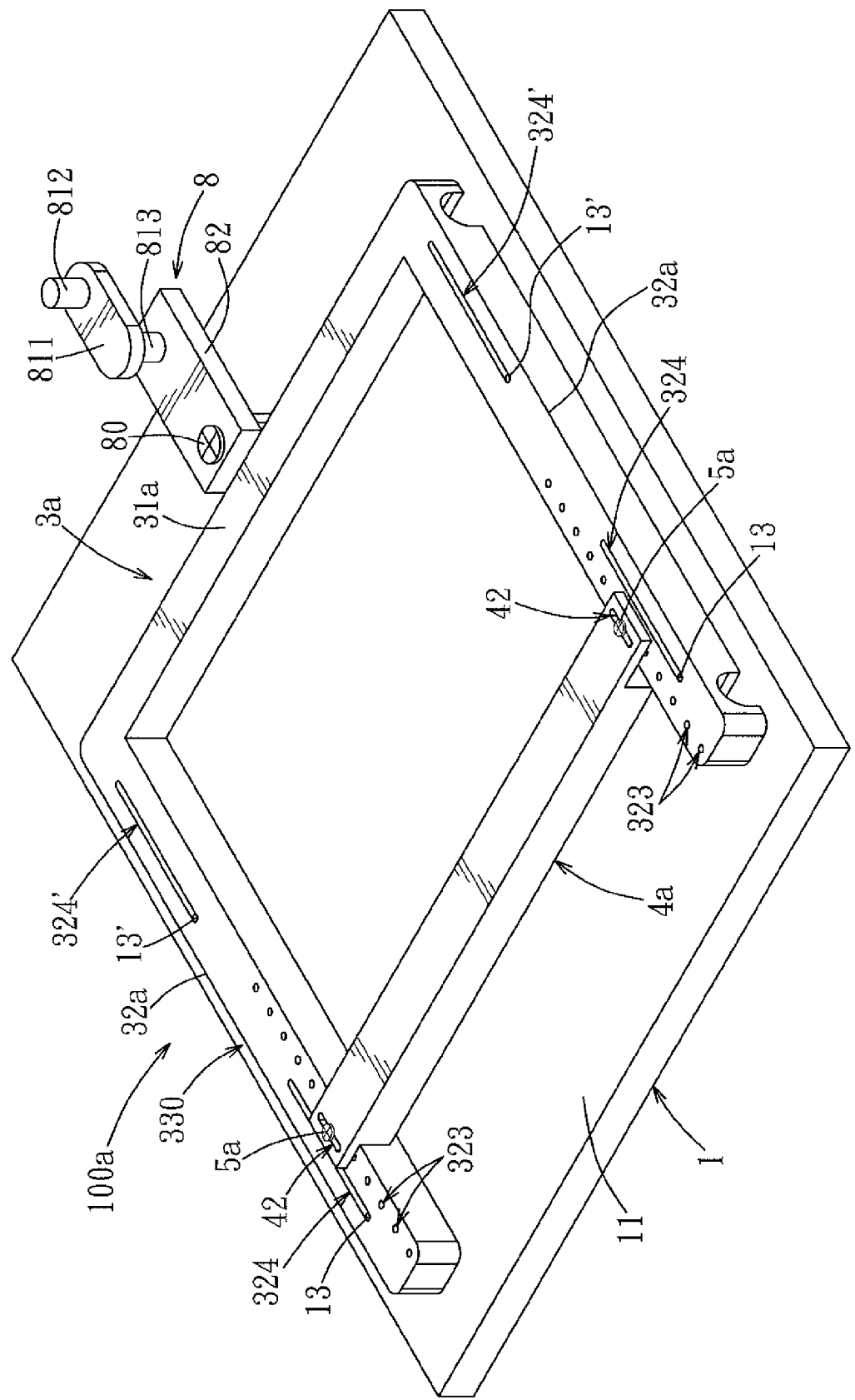
FIG. 13 is a perspective view of a friction testing device having a clamping jig according to the fourth embodiment of the present disclosure.
Figure 14:
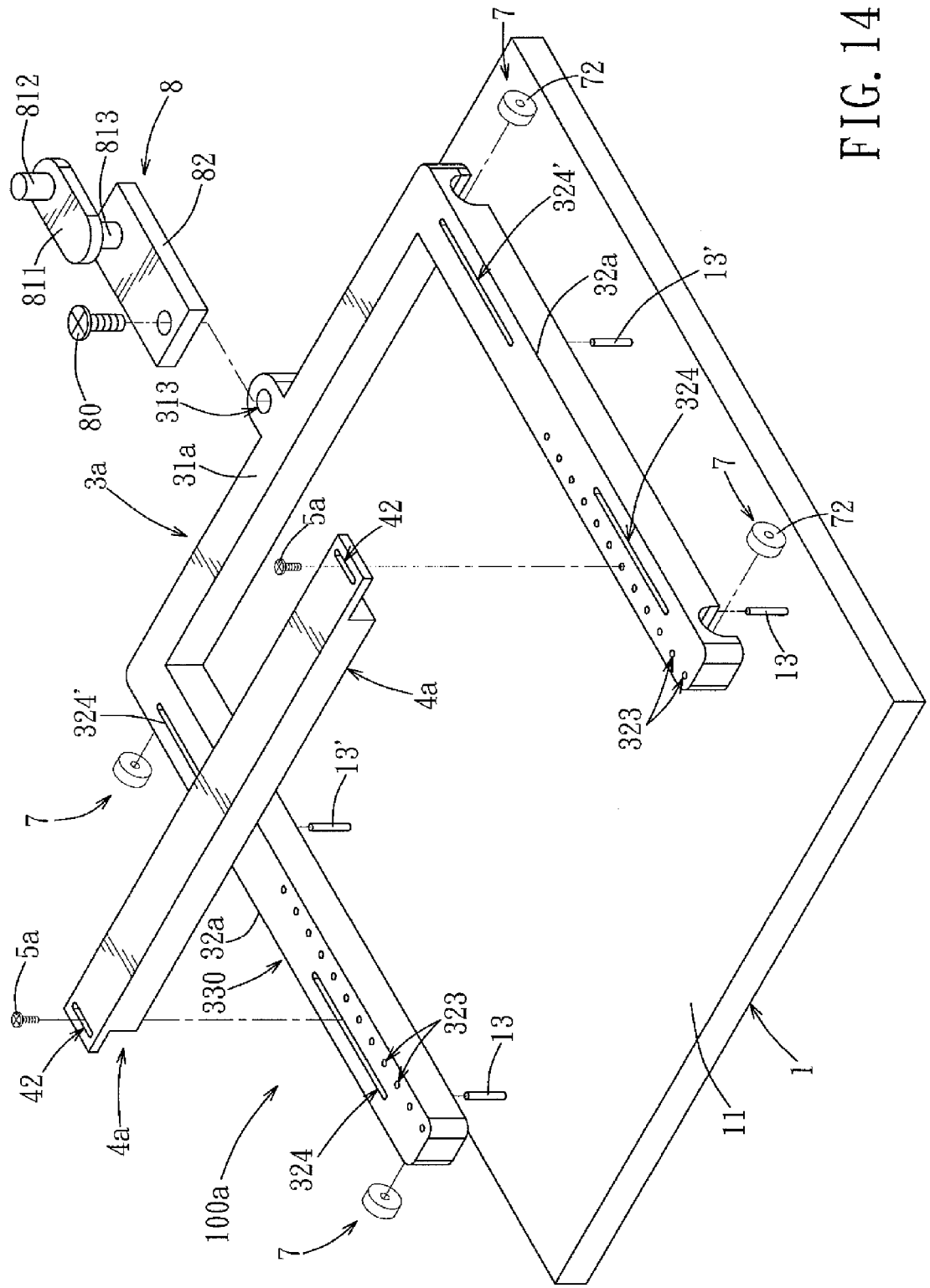
FIG. 14 is an exploded perspective view of the fourth embodiment.
Figure 15:
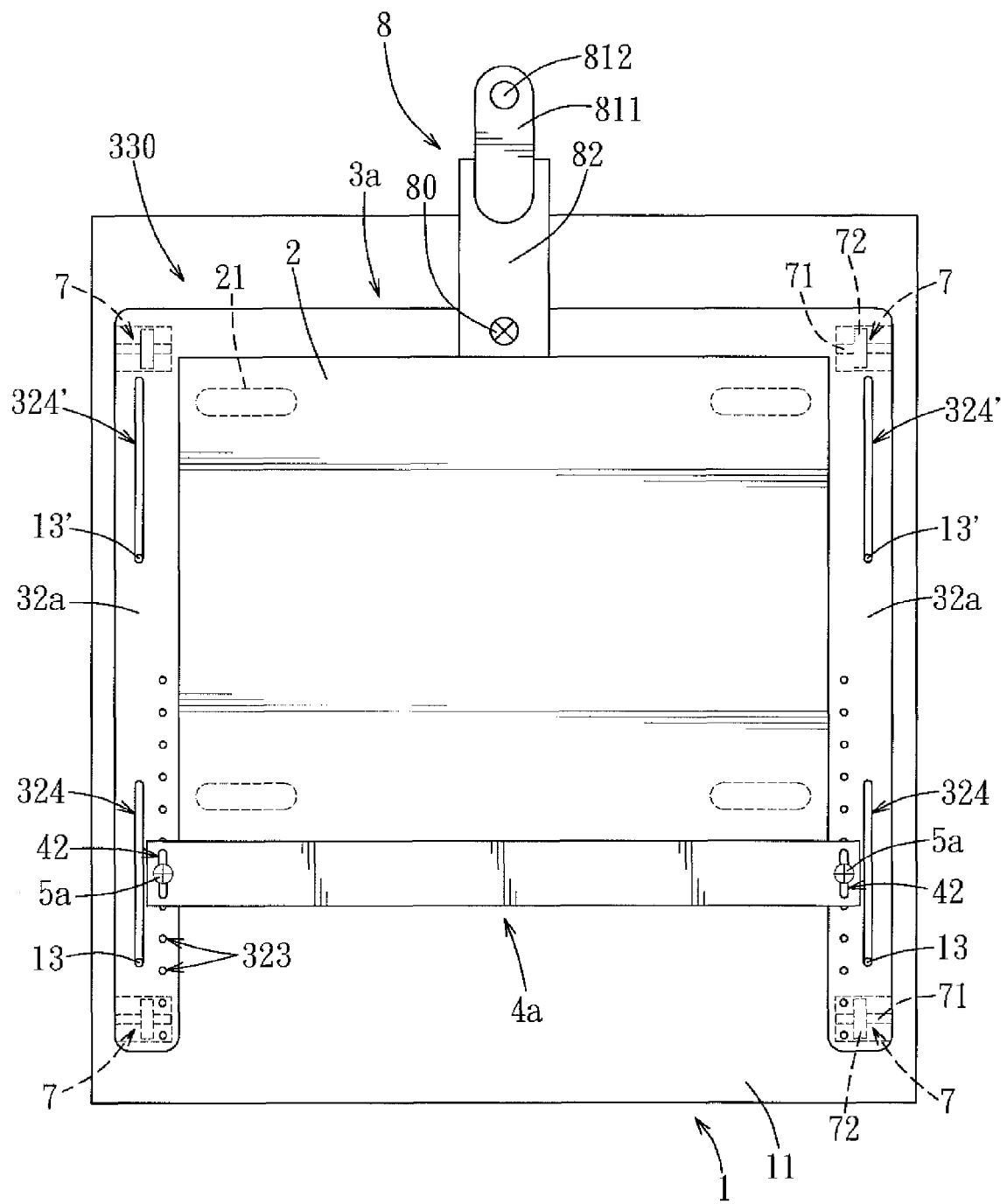
FIG. 15 is a schematic top view of the fourth embodiment in an assembled state.

Referring to FIGS. 13 to 15, a friction testing device (100a) according to the fourth embodiment of the present disclosure has a structure and an operating method similar to that described in the second embodiment. The difference between the fourth and second embodiments resides in the construction of the clamping frame 3' of the clamping jig 330.

In this embodiment, the second clamping members (32a) are connected integrally as one piece to the first clamping member (31a). Each second clamping member (32a) includes a plurality of screw holes 323 spaced apart from each other in the length direction of the second clamping members 32. The third clamping member (4a) is rectangular, has left and right ends respectively overlapping the second clamping elements (32a), and includes two passage holes 42 formed respectively in the left and right ends thereof. Each first positioning element (5a) is configured as a screw that extends through the passage hole 42 in one of the left and right ends of the third clamping member (4a) and that engages a selected one of the screw holes 323 in a respective second clamping member (32a), which is aligned with the selected one of the screw holes 323. As such, the third clamping member (4a) can be positioned on and disposed between the second clamping members (32a). Each passage hole 42 is elongated in a direction that is transverse to a length direction of the third clamping member (4a) so that the third clamping member (4a) is movable relative to the first positioning element (5a) along the direction of the passage holes 42 to adjust the third clamping member (4a) slightly within an elongated range of each passage hole 42.

Further, in this embodiment, the limit unit includes two first limit pins 13 upstanding from the top frictional face 11 in proximity to the front side of the working platform 1 and spaced apart in the left-right direction, and two second limit pins 13' upstanding from the top frictional face 11 and respectively spaced apart from the first limit pins 13' in the front-rear direction. Each second clamping member (32a) further includes first and second slide holes 324 spaced apart from each other in the front-rear direction. Each of the first and second slide holes 324, 324' extends in the length direction of the second clamping members (32a). The first guide pins 13 extend movably and respectively into the first slide holes 321 in the second clamping members (32a). The second guide pins 13' extend movably and respectively into the second slide holes 324, 324' in the second clamping members (32a). Because the first and second guide pins 13, 13' are restricted to move within the respective first and second slide holes 324, 324', the clamping jig 330 can only move the test object 2 in one single direction to satisfy a friction test condition for the test object 2 moving in a single direction.

Figure 16:
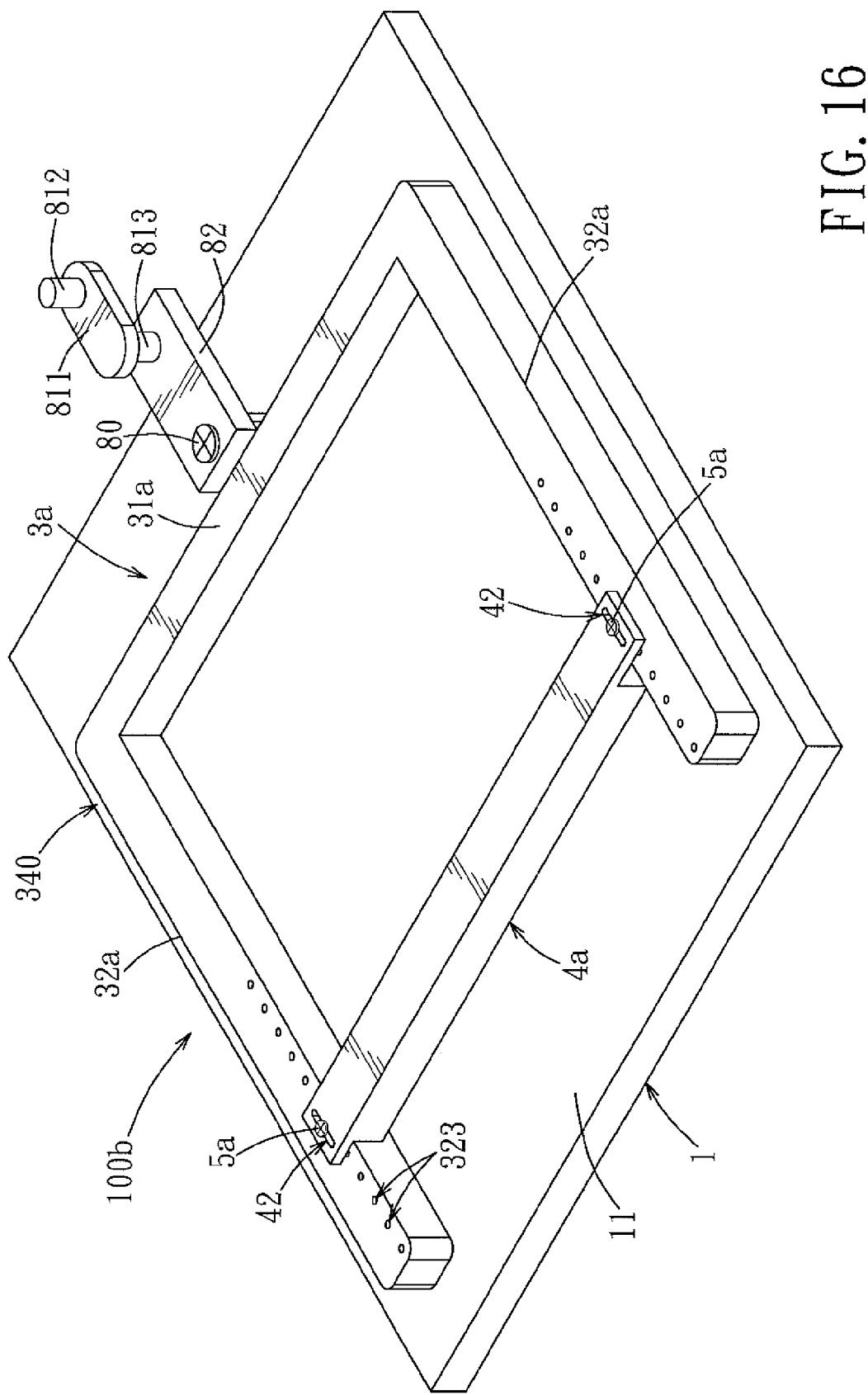
FIG. 16 is a perspective view of a friction testing device having a clamping jig according to the fifth embodiment of the present disclosure.
Figure 17:
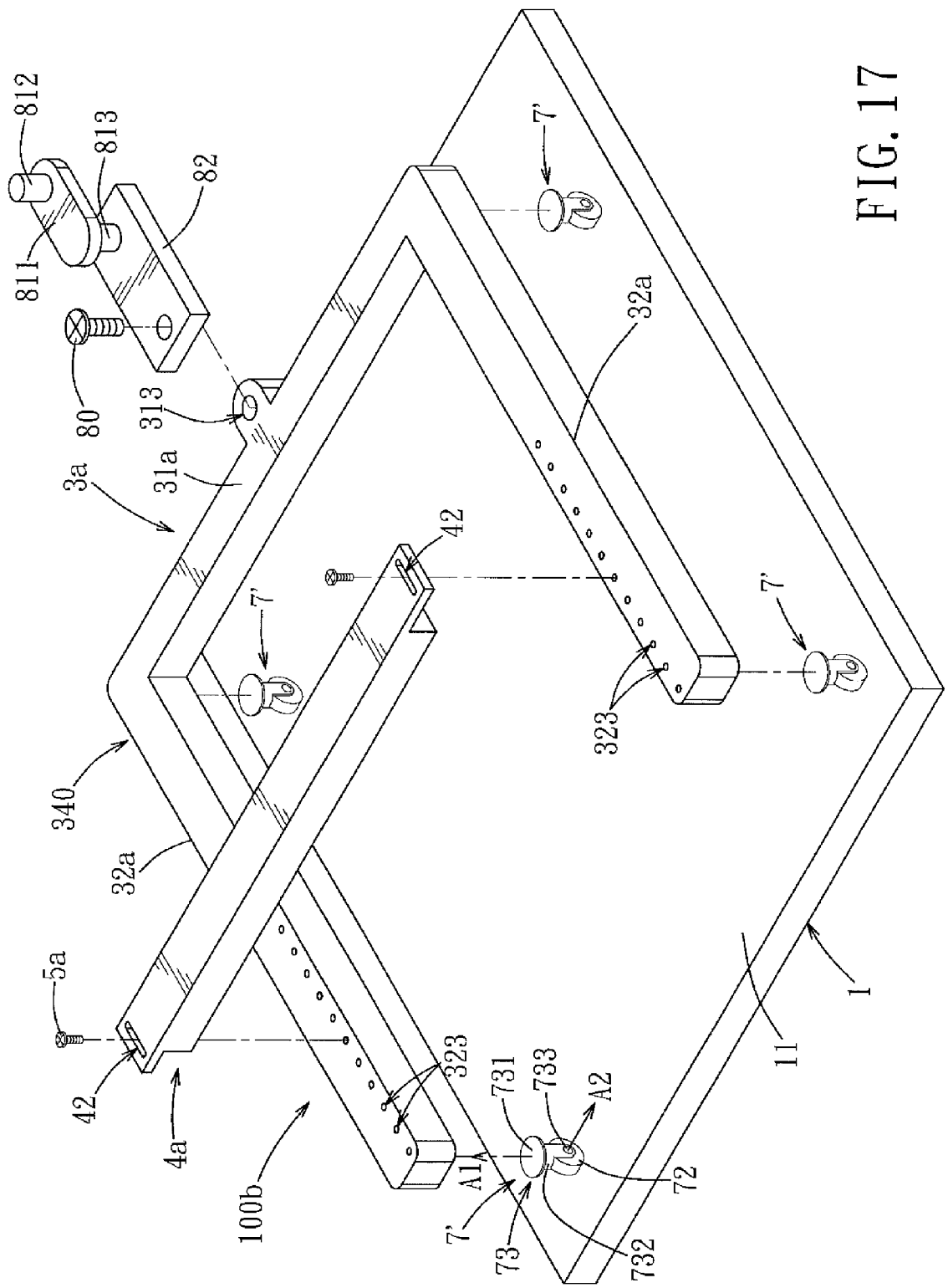
FIG. 17 is an exploded perspective view of the fifth embodiment.
Figure 18:
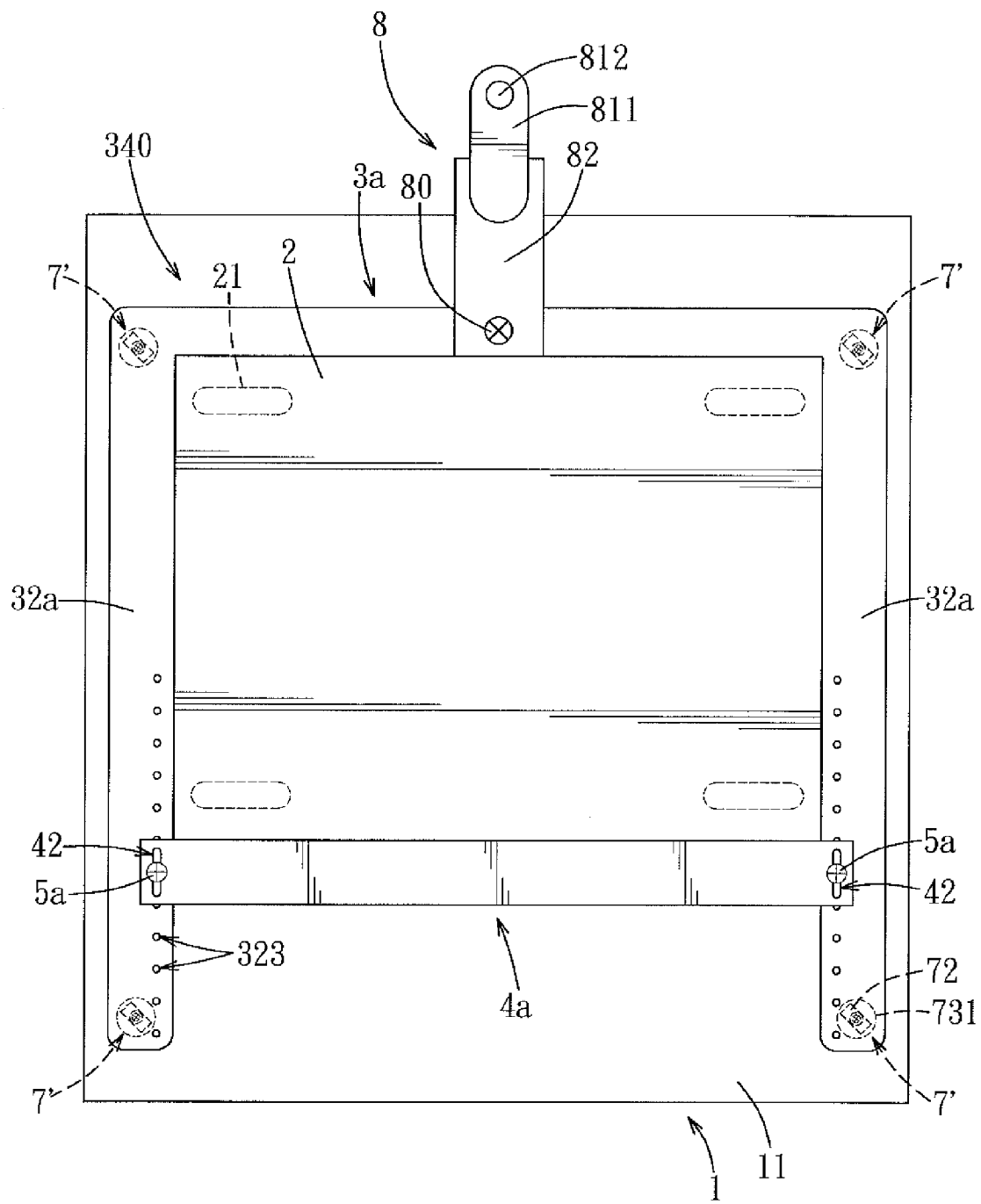
FIG. 18 is a schematic top view of the fifth embodiment in an assembled state.

Referring to FIGS. 16 to 18, a friction testing device (100b) according to the fifth embodiment of the present disclosure has a structure and an operating method similar to that described in the fourth embodiment. The difference between the fourth and fifth embodiments resides in that the structure of the roller units 7' of the clamping jig 340 is similar to that described in the third embodiment.

Further, in this embodiment, the top frictional face 11 of the working platform 1 is dispensed with the first and second guide pins 13, 13' (see FIG. 14), and each second clamping member (32a) of the clamping frame (3a) of the clamping jig 340 is dispensed with the first and second slide holes 324, 324' (see FIG. 14). Because the roller units 7' are configured as swivel rollers, the clamping jig 340 can move the test object 2 in any direction. This simulates movement of the test object 2 in any direction during actual use thereof, and satisfies a friction test condition for the test object 2 moving in any direction.

From the aforesaid description, through the configuration of the clamping frame (3, 3a) of the clamping jig 300, 310, 320, 330, 340 of the friction testing device 100, 100', 100", (100a), (100b) in each embodiment, test objects having different specifications and dimensions can be clamped, thereby increasing the flexibility of use of the friction testing device 100, 100', 100", (100a), (100b), so that friction tests of the test objects having different specifications and dimensions can be performed. Further, through the configuration of the roller units 7, 7', a frictional force between the clamping jig 310, 320 330, 340 and the top frictional face 11 can be reduced, thereby lowering the effect of the frictional force on the foot pads 21 of the test object 2 during friction testing, and thereby enhancing accuracy of the friction test. Moreover, movement of the test object 2 in any direction during actual use thereof can be simulated to ensure conformity of the friction test method to the actual use and to enhance reliability of the test object. Hence, the objects of the present disclosure can be realized.

While the present disclosure has been described in connection with what are considered the most practical and embodiments, it is understood that this disclosure is not limited to the disclosed embodiments but is intended to cover various arrangements included within the spirit and scope of the broadest interpretations and equivalent arrangements.

We claim:

1. A clamping jig for clamping a test object, comprising:
a first clamping member extending in a left-right direction;
two second clamping members connected to and extending transversely of said first clamping member and spaced apart from each other in the left-right direction; and
a third clamping member connected to and extending transversely of said second clamping members, said third clamping member being movable along said second clamping members in a front-rear direction to adjust a distance between said first and third clamping members, said first, second, and third clamping members being adapted to clamp therebetween the test object.

2. The clamping jig of claim 1, wherein one of said second clamping members is movable relative to said first clamping member and said third clamping member in the left-right direction to adjust a distance between said two second clamping members.

3. The clamping jig of claim 1, further comprising a plurality of spaced-apart roller units attached to bottom ends of said first and second clamping members.

4. The clamping jig of claim 2, further comprising two first positioning elements to position said third clamping member on said second clamping members, and a second positioning element to position said one of said second clamping members on said first clamping member.

5. The clamping jig of claim 4, wherein said third clamping member has an elongated guide hole extending in the left-right direction, each of said second clamping members extending through said guide hole to intersect said third clamping member and including an elongated positioning hole that extends in the front-rear direction, each of said first positioning elements extending through said positioning hole and positioning said third clamping member to one of said second clamping members.

6. The clamping jig of claim 5, wherein said positioning hole communicates with said guide hole, each of said first positioning elements including a screw that extends through said guide hole and said positioning hole and that has a screw head, and a nut engaged to said screw opposite to said screw head, said third clamping member being engaged between said screw head and said nut.

7. The clamping jig of claim 4, wherein said first clamping member includes a plurality of screw holes extending therethrough in a top-bottom direction and spaced apart from each other in the left-right direction, said one of said second clamping members further including a through hole alignable with one of said screw holes in said first clamping member, said second positioning element being configured as a screw that engages one of said screw holes in said first clamping member and that extends through said through hole in said one of said second clamping members.

8. The clamping jig of claim 7, wherein said through hole in said one of said second clamping members is elongated in the left-right direction, said one of said second clamping members being movable relative to said second positioning element along an extending direction of said through hole, said first clamping member further including an elongated guide groove that receives one end of each of said second clamping members and that communicates with said screw holes in said first clamping member and said through hole in said one of said second clamping members, said guide groove in said first clamping member and said guide hole in said third clamping member being at a same height from said working platform.

9. The clamping jig of claim 1, wherein each of said second clamping members includes a plurality of screw holes spaced apart from each other in a length direction of said second clamping members, said third clamping member having left and right ends respectively overlapping said second clamping members and including spaced-apart passage holes formed respectively in said left and right ends, said clamping jig further including two first positioning elements, each of said first positioning elements being configured as a screw that extends through one of said passage holes and that engages a selected one of said screw holes in one of said second clamping members, which is aligned with said one of said passage holes.

10. The clamping jig of claim 9, wherein each of said passage holes is elongated in a direction that is transverse to a length direction of said third clamping member so that said third clamping member is movable relative to said first positioning elements along said direction of said passage holes.

11. A friction testing device for a test object, comprising:
a working platform including a top frictional face;
a clamping jig having a clamping frame that is disposed movably on said top frictional face and that includes
a first clamping member extending in a left-right direction,
two second clamping members connected to and extending transversely of said first clamping member and spaced apart from each other in the left-right direction, and
a third clamping member connected to and extending transversely of said second clamping members, said third clamping member being movable along said second clamping members in a front-rear direction to adjust a distance between said first and third clamping members, said first, second, and third clamping members being adapted to clamp therebetween the test object; and
a push mechanism to move reciprocally said clamping jig on said top frictional face.

12. The friction testing device of claim 11, wherein one of said second clamping members is movable relative to said first clamping member and said third clamping member in the left-right direction to adjust a distance between said two second clamping members.

13. The friction testing device of claim 11, wherein said clamping jig further includes a plurality of spaced-apart roller units attached to a bottom side of said clamping frame.

14. The friction testing device of claim 13, wherein said roller units are attached to bottom sides of said first and second clamping members.

15. The friction testing device of claim 14, wherein said roller units are configured as swivel rollers, each of said swivel rollers including a roller, and a connector connecting said roller to one of said first and second clamping members, said connector having a first rotation axis extending in a top-bottom direction, and a second rotation axis perpendicular to said first rotation axis, said roller being rotatable about said first and second rotation axes.

16. The friction testing device of claim 12, wherein said clamping jig further includes two first positioning elements to position said third clamping member on said second clamping members, and a second positioning element to position said one of said second clamping members on said first clamping member.

17. The friction testing device of claim 16, wherein said third clamping member includes an elongated guide hole extending in the left-right direction, each of said second clamping members extending through said guide hole to intersect said third clamping member and including an elongated positioning hole that extends in the front-rear direction, each of said first positioning elements extending through said positioning hole and positioning said third clamping member to one of said second clamping members.

18. The friction testing device of claim 17, wherein said positioning hole communicates with said guide hole, each of said first positioning elements including a screw that extends through said guide hole and said positioning hole and that has a screw head, and a nut engaged to said screw opposite to said screw head, said third clamping member being engaged between said screw head and said nut.

19. The friction testing device of claim 16, wherein said first clamping member includes a plurality of screw holes extending therethrough in a top-bottom direction and spaced apart from each other in the left-right direction, said one of said second clamping members further including a through hole alignable with one of said screw holes in said first clamping member, said second positioning element being configured as a screw that engages one of said screw holes in said first clamping member and that extends through said through hole in said one of said second clamping members.

20. The friction testing device of claim 19, wherein said through hole in said one of said second clamping member is elongated in the left-right direction, said one of said second clamping members being movable relative to said second positioning element along an extending direction of said through hole, said first clamping member further including an elongated guide groove that receives one end of each of said second clamping members and that communicates with said screw holes in said first clamping member and said through hole in said one of said second clamping members, said guide groove in said first clamping member and said guide hole in said third clamping member being at a same height from said working platform.

21. The friction testing device of claim 11, wherein each of said second clamping members includes a plurality of screw holes spaced apart from each other in a length direction of said second clamping members, said third clamping member having left and right ends respectively overlapping said second clamping members and including two spaced-apart passage holes formed respectively in said left and right ends, said clamping jig further including two first positioning elements, each of said first positioning elements being configured as a screw that extends through one of said passage holes and that engages a selected one of said screw holes in one of said second clamping members, which is aligned with said one of said passage holes.

22. The friction testing device of claim 21, wherein each of said passage holes is elongated in a direction that is transverse to a length direction of said third clamping member so that said third clamping member is movable relative to said first positioning elements along said direction of said passage holes.

23. The friction testing device of claim 22, wherein said working platform further includes left and right sides, front and rear sides, and a limit unit disposed on said top frictional face to limit said clamping frame to move in a front-rear direction along said top frictional face.

24. The friction testing device of claim 23, wherein said limit unit includes two spaced-apart guide rails extending in the front-rear direction, said first clamping member having left and right ends in sliding contact with said guide rails, respectively.

25. The friction testing device of claim 23, wherein said limit unit includes two limit pins upstanding from said top frictional face and spaced apart in the left-right direction, each of said second clamping members further including a slide hole extending in the length direction of said second clamping members, said limit pins extending respectively into said slide holes in said second clamping members.

26. The friction testing device of claim 21, wherein said clamping jig further includes a plurality of roller units attached to bottom ends of said first and second clamping members.

* * * * *